(12) United States Patent
Ash et al.

(10) Patent No.: US 10,324,350 B2
(45) Date of Patent: Jun. 18, 2019

(54) COLOR EXCURSION MITIGATION IN ELECTROCHROMIC DEVICES

(71) Applicant: Gentex Corporation, Zeeland, MI (US)

(72) Inventors: Kevin L. Ash, Grand Rapids, MI (US); Kelvin L. Baumann, Holland, MI (US)

(73) Assignee: GENTEX CORPORATION, Zeeland, MI (US)

( * ) Notice: Subject to any disclaimer, the term of this patent is extended or adjusted under 35 U.S.C. 154(b) by 70 days.

(21) Appl. No.: 15/718,441

(22) Filed: Sep. 28, 2017

(65) Prior Publication Data

US 2018/0095338 A1 Apr. 5, 2018

Related U.S. Application Data

(60) Provisional application No. 62/402,315, filed on Sep. 30, 2016, provisional application No. 62/411,924, filed on Oct. 24, 2016.

(51) Int. Cl.
*C09K 9/02* (2006.01)
*B32B 17/10* (2006.01)
(Continued)

(52) U.S. Cl.
CPC .............. *G02F 1/1503* (2019.01); *C09K 9/02* (2013.01); *G02F 1/153* (2013.01); *G02F 1/161* (2013.01);
(Continued)

(58) Field of Classification Search
CPC ........... C09K 9/02; G02F 1/15; G02F 1/1503; G02F 1/1514; G02F 1/1523; G02F 1/153; G02F 1/15165; G02F 1/155; G02F 1/161; G02F 2001/1502; G02F 1/15145; C07D 213/22; C07D 241/36; C07D 241/46;
(Continued)

(56) References Cited

U.S. PATENT DOCUMENTS 4,297,401 A 10/1981 Chern et al.
4,418,102 A 11/1983 Ferrato
(Continued)

FOREIGN PATENT DOCUMENTS

| WO | WO-98/42796 A1 | 10/1998 |
| WO | WO-99/02621 A1 | 1/1999 |
| WO | WO-2008/150851 A1 | 12/2008 |

OTHER PUBLICATIONS

International Search Report and Written Opinion on International Application No. PCT/US2017/054050 dated Dec. 21, 2017 (7 pages).

*Primary Examiner* — Loha Ben
(74) *Attorney, Agent, or Firm* — Foley & Lardner LLP; Bradley D. Johnson (57) ABSTRACT

An electrochromic device includes a chamber defined by a first conductive surface of a first substrate, a second conductive surface of a second substrate, and a sealing member joining the first substrate to the second substrate; an electrochromic medium containing a blue cathodic electroactive compound and up to three anodic electroactive compounds; wherein the electrochromic medium is disposed within the chamber; the anodic electroactive compounds include a green anodic electroactive compound and one or two gray anodic electroactive compounds; and the anodic electroactive compounds include from about 8 mol % to about 15 mol % gray anodic electroactive compounds.

20 Claims, 3 Drawing Sheets

(51) Int. Cl.
*C07D 241/46* (2006.01)
*G02F 1/15* (2019.01)
*G02F 1/161* (2006.01)
*G09G 3/38* (2006.01)
*G02F 1/1503* (2019.01)
*G02F 1/153* (2006.01)
*G02F 1/1516* (2019.01)
*G02F 1/1514* (2019.01)

(52) U.S. Cl.
CPC .......... *G09G 3/38* (2013.01); *B32B 17/10513* (2013.01); *C07D 241/46* (2013.01); *G02F 1/1514* (2019.01); *G02F 1/15165* (2019.01); *G02F 2001/15145* (2019.01)

(58) Field of Classification Search
CPC ........ B32B 17/10165; B32B 17/10467; B32B 17/10513; G09G 3/38
USPC .......... 359/265–275; 345/105; 252/500, 582, 252/583, 586; 544/347
See application file for complete search history.

(56) References Cited

U.S. PATENT DOCUMENTS

| | | |
|---|---|---|
| 4,695,490 A | 9/1987 | McClelland et al. |
| 4,830,471 A * | 5/1989 | Demiryont ............ G02F 1/1523 359/265 |
| 4,902,108 A | 2/1990 | Byker |
| 5,596,023 A | 1/1997 | Tsubota et al. |
| 5,596,024 A | 1/1997 | Horie et al. |
| 5,818,625 A | 10/1998 | Forgette et al. |
| 5,928,572 A | 7/1999 | Tonar et al. |
| 5,998,617 A * | 12/1999 | Srinivasa ............ C07D 213/22 544/347 |
| 6,020,987 A * | 2/2000 | Baumann .......... B32B 17/10036 359/273 |
| 6,037,471 A * | 3/2000 | Srinivasa ............ C07D 213/22 546/257 |
| 6,141,137 A * | 10/2000 | Byker .................. C07D 213/22 359/265 |
| 6,157,480 A | 12/2000 | Anderson et al. |
| 6,188,505 B1 | 2/2001 | Lomprey et al. |
| 6,597,489 B1 | 7/2003 | Guarr et al. |
| 6,635,194 B2 | 10/2003 | Kloeppner et al. |
| 6,700,692 B2 | 3/2004 | Tonar et al. |
| 6,710,906 B2 | 3/2004 | Guarr et al. |
| 6,714,334 B2 | 3/2004 | Tonar |
| 7,046,418 B2 | 5/2006 | Lin et al. |
| 7,372,611 B2 | 5/2008 | Tonar et al. |
| 7,450,292 B1 * | 11/2008 | Burrell .................... B60R 1/088 359/270 |
| 7,855,821 B2 | 12/2010 | Baumann et al. |
| 2002/0118437 A1 | 8/2002 | Rukavina et al. |

* cited by examiner

COLOR EXCURSION MITIGATION IN ELECTROCHROMIC DEVICES

CROSS-REFERENCE TO RELATED APPLICATIONS

This application claims the benefit of priority to U.S. Provisional Application No. 62/411,924, filed on Oct. 24, 2016, and U.S. Provisional Application No. 62/402,315, filed on Sep. 30, 2016, both of which are incorporated by reference herein in their entirety.

BACKGROUND

The present invention relates generally to the field of electrochromic devices and apparatuses incorporating these devices. More particularly, the technology relates to color excursion mitigation of these devices.

SUMMARY

Provided herein, in one aspect, are electrochromic devices containing a chamber defined by a first conductive surface of a first substrate, a second conductive surface of a second substrate, and a sealing member joining the first substrate to the second substrate; an electrochromic medium containing a blue cathodic electroactive compound and up to three anodic electroactive compounds; wherein the electrochromic medium is disposed within the chamber; the anodic electroactive compounds include a green anodic electroactive compound and one or two gray anodic electroactive compounds; and the anodic electroactive compounds contains from about 8 mol % to about 15 mol % gray anodic electroactive compounds. In some embodiments, the electrochromic device, in a low transmission state, exhibits a u'-v' color space having a u' value from about 0.15 to about 0.30 and a v' value from about 0.30 to about 0.40. In some embodiments, the u' value is from about 0.18 to about 0.22. In some embodiments, the anodic electroactive compounds include one green anodic electroactive compound and two gray anodic electroactive compounds. In some embodiments, the gray anodic electroactive compounds are selected from 2,7-diisobutyl-5,10-dineopentyl-5,10-dihydrophenazine; 2,7-di-2-ethylbutyl-5,10-dineopentyl-5,10-dihydrophenazine; 2,7-di-2-ethylhexyl-5,10-dineopentyl-5,10-dihydrophenazine; and 2,5,7,10-tetraneopentyl-5,10-dihydrophenazine. In some embodiments, the blue cathodic electroactive compound is an alkyl viologen. In some embodiments, the alkyl viologen is selected from 1,1'-bis-2-ethylhexyl-4,4-bipyridinium tetrafluoroborate, 1,1'-bis-isobutyl-4,4'-bipyridinium tetrafluoroborate; and 1,1'-bis 2-ethyl butyl-4,4'-bipyridinium tetrafluoroborate. In some embodiments, the green anodic electroactive compound is 5,10-dihydro-5,10-dineopentylphenazine; 5,10-[2(ethyl)butyl]-5,10-dihydrophenazine; or 5,10-[2(ethyl)hexyl]-5,10-dihydrophenazine. In some embodiments, the molar ratio of the cathodic electroactive compound to the anodic electroactive compounds is about 1:1 to about 1.1:1. In some embodiments, the electrochromic device further includes one or more UV stabilizers. In further embodiments, the one or more UV stabilizers are selected from 2-ethyl-2-cyano-3,3-diphenyl acrylate; (2-ethylhexyl)-2-cyano-3,3-diphenyl acrylate; 2-(2'-hydroxy-4'-methylphenyl)benzotriazole; 3-[3-(2H-benzotriazole-2-yl)-5-(1,1-dimethylethyl)-4-hydroxyphenyl]propionic acid pentyl ester; a composition of $C_{7-9}$ branched and linear alkyl esters of 3-(2H-benzotriazol-2-yl)-5-(1,1-dimethylethyl)-4-hydroxy-benzenepropanoic acid and 1-methoxy-2-propylacetate; 2,4-dihydroxybenzophenone; 2-hydroxy-4-methoxybenzophenone; and 2-ethyl-2'-ethoxyalanilide. In some embodiments, the electrochromic device further includes an anodic and/or cathodic color-stabilizing redox buffer. In some embodiments, the electrochromic device further includes a cross-linked polymer matrix, a free-standing gel, and/or a substantially non-weeping gel. In some embodiments, the electrochromic device has a clear state and a darkened state and the electrochromic medium maintains a blue-gray color in the darkened state. In further embodiments, the blue-gray color is devoid of a purple hue as observed by the naked eye. In some embodiments, the electrochromic device is an electrochromic aircraft transparency.

Provided herein, in another aspect, are electrochromic devices containing an electrochromic medium containing a blue cathodic electroactive compound and up to three anodic electroactive compounds; wherein the anodic electroactive compounds include a green anodic electroactive compound and one or two gray anodic electroactive compounds; and the electrochromic device, in a low transmission state, exhibits a u'-v' color space having a u' value from about 0.15 to about 0.30 and a v' value from about 0.30 to about 0.40. In some embodiments, the u' value is from about 0.18 to about 0.22. In some embodiments, the anodic electroactive compounds include one green anodic electroactive compound and two gray anodic electroactive compounds. In some embodiments, the gray anodic electroactive compounds are selected from 2,7-diisobutyl-5,10-dineopentyl-5,10-dihydrophenazine; 2,7-di-2-ethylbutyl-5,10-dineopentyl-5,10-dihydrophenazine; 2,7-di-2-ethylhexyl-5,10-dineopentyl-5,10-dihydrophenazine; and 2,5,7,10-tetraneopentyl-5,10-dihydrophenazine. In some embodiments, the blue cathodic electroactive compound is an alkyl viologen. In some embodiments, the alkyl viologen is selected from 1,1'-bis-2-ethylhexyl-4,4-bipyridinium tetrafluoroborate, 1,1'-bis-isobutyl-4,4'-bipyridinium tetrafluoroborate; and 1,1'-bis 2-ethyl butyl-4,4'-bipyridinium tetrafluoroborate. In some embodiments, the green anodic electroactive compound is 5,10-dihydro-5,10-dineopentylphenazine; 5,10-[2(ethyl)butyl]-5,10-dihydrophenazine; or 5,10-[2(ethyl)hexyl]-5,10-dihydrophenazine. In some embodiments, the molar ratio of the cathodic electroactive compound to the anodic electroactive compounds is about 1:1 to about 1.1:1. In some embodiments, the electrochromic device further includes one or more UV stabilizers. In further embodiments, the one or more UV stabilizers are selected from 2-ethyl-2-cyano-3,3-diphenyl acrylate; (2-ethylhexyl)-2-cyano-3,3-diphenyl acrylate; 2-(2'-hydroxy-4'-methylphenyl)benzotriazole; 3-[3-(2H-benzotriazole-2-yl)-5-(1,1-dimethylethyl)-4-hydroxyphenyl]propionic acid pentyl ester; a composition of $C_{7-9}$ branched and linear alkyl esters of 3-(2H-benzotriazol-2-yl)-5-(1,1-dimethylethyl)-4-hydroxy-benzenepropanoic acid and 1-methoxy-2-propylacetate; 2,4-dihydroxybenzophenone; 2-hydroxy-4-methoxybenzophenone; and 2-ethyl-2'-ethoxyalanilide. In some embodiments, the electrochromic device further includes an anodic and/or cathodic color-stabilizing redox buffer. In some embodiments, the electrochromic device further includes a cross-linked polymer matrix, a free-standing gel, and/or a substantially non-weeping gel. In some embodiments, the electrochromic device has a clear state and a darkened state and the electrochromic medium maintains a blue-gray color in the darkened state. In further embodiments, the blue-gray color is devoid of a purple hue as observed by the naked eye. In some embodiments, the electrochromic device is an electrochromic aircraft transparency.

Provided herein, in another aspect, are methods to minimize or remove purple hue from an electrochromic medium within an electrochromic device in the darkened state, the method including adjusting the concentration of gray anodic electroactive compound to from about 8 mol % to about 15 mol % relative to the total molar concentration of anodic electroactive compounds. In some embodiments, the gray anodic electroactive compound includes one or more selected from 2,7-diisobutyl-5,10-dineopentyl-5,10-dihydrophenazine; 2,7-di-2-ethylbutyl-5,10-dineopentyl-5,10-dihydrophenazine; 2,7-di-2-ethylhexyl-5,10-dineopentyl-5,10-dihydrophenazine; and 2,5,7,10-tetraneopentyl-5,10-dihydrophenazine.

BRIEF DESCRIPTION OF THE DRAWINGS

The disclosure will become more fully understood from the following detailed description, taken in conjunction with the accompanying figure, in which.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Electrochromic devices can be used in a wide variety of applications wherein the transmitted or reflected light/heat can be modulated. Such devices include mirrors; aircraft transparencies; windows for the exterior of a building, home or vehicle; skylights for buildings including tubular light filters; windows in office or room partitions; and light filters for photographic devices and light sensors.

The electrochromic medium within many electrochromic devices exhibits variable transmittance. As the electrochromic medium is electrically energized, it darkens and begins to absorb light. When the applied electrical voltage is decreased to zero, the medium returns to its clear state. In general, there is a desire for a neutral-colored electrochromic medium in the darkened state. Typically, the neutral color is blue or gray hue, or a combination thereof, as observed by the naked eye. Deviation from the desired neutral color is described herein as "color excursion." In some embodiments, the color excursion is a purple hue as observed by the naked eye.

Provided herein, in one aspect, are electrochromic devices that mitigate color excursion. In some embodiments, the electrochromic device contains an electrochromic medium containing a blue cathodic electroactive compound and up to three anodic electroactive compounds. In further embodiments, the anodic electroactive compounds include a green anodic electroactive compound and one or two gray anodic electroactive compounds. In some embodiments, the electrochromic device has a clear state and a darkened state and the electrochromic medium maintains a blue-gray color in the darkened state. In some embodiments, the blue-gray color is devoid of a purple hue as observed by the naked eye. In some embodiments, the electrochromic device, in a low transmission state, exhibits a u'-v' color space having a u' value from about 0.15 to about 0.30 and a v' value from about 0.30 to about 0.40. In some embodiments, the u' value is from about 0.18 to about 0.22.

Provided herein, in another aspect, are electrochromic devices containing an electrochromic medium comprising a blue cathodic electroactive compound and up to three anodic electroactive compounds; wherein the anodic electroactive compounds comprise a green anodic electroactive compound and one or two gray anodic electroactive compounds; and the electrochromic device, in a low transmission state, exhibits a u'-v' color space having a u' value from about 0.15 to about 0.30 and a v' value from about 0.30 to about 0.40. In some embodiments, the u' value is from about 0.18 to about 0.22.

Provided herein, in another aspect, are electrochromic devices containing a chamber defined by a first conductive surface of a first substrate, a second conductive surface of a second substrate, and a sealing member joining the first substrate to the second substrate; an electrochromic medium containing a blue cathodic electroactive compound and up to three anodic electroactive compounds; wherein the electrochromic medium is disposed within the chamber; the anodic electroactive compounds include a green anodic electroactive compound and one or two gray anodic electroactive compounds; and the anodic electroactive compounds contains from about 8 mol % to about 15 mol % gray anodic electroactive compounds. The electrochromic device may further contain one or more UV stabilizers, an anodic color-stabilizing redox buffer, and/or a cathodic color-stabilizing redox buffer. In some embodiments, the electrochromic device further includes a cross-linked polymer matrix, a free-standing gel, and/or a substantially non-weeping gel. The electrochromic devices described herein exhibit a high transmission (i.e., clear) state and a low transmission (i.e., darkened) state, where the electrochromic medium maintains a blue, gray, or blue-gray color in the low transmission state. In some embodiments, the blue-gray color is devoid of a purple hue as observed by the naked eye. In some embodiments, the electrochromic device is an electrochromic aircraft transparency.

As used herein, a "blue cathodic electroactive compound" does not substantially absorb blue light in the 450 to 495 nm range. For example, an electrochromic medium containing a blue cathodic electroactive compound will allow at least 80% of blue light in the 450 to 495 nm range to be transmitted through the medium, provided there is/are no other compound(s) in the medium that absorb(s) the blue light. In some embodiments, an electrochromic medium containing a blue cathodic electroactive compound will allow at least 85%, at least 90%, or at least 95% of blue light in the 450 to 495 nm range to be transmitted through the medium, provided there is/are no other compound(s) in the medium that absorb(s) the blue light.

As used herein, a "green anodic electroactive compound" does not substantially absorb green light in the 495 to 570 nm range. For example, an electrochromic medium containing a green cathodic electroactive compound will allow at least 80% of green light in the 495 to 570 nm range to be transmitted through the medium, provided there is/are no other compound(s) in the medium that absorb(s) the green light. In some embodiments, an electrochromic medium containing a green cathodic electroactive compound will allow at least 85%, at least 90%, or at least 95% of green light in the 495 to 570 nm range to be transmitted through the medium, provided there is/are no other compound(s) in the medium that absorb(s) the green light.

As used herein, a "gray anodic electroactive compound" does not substantially absorb red light in the 620 to 750 nm range and yellow light in the 570 to 590 nm range. For example, an electrochromic medium containing a gray cathodic electroactive compound will allow at least 80% of red light in the 620 to 750 nm range and at least 80% of yellow light in the 570 to 590 nm range to be transmitted through the medium, provided there is/are no other compound(s) in the medium that absorb(s) the red light and/or yellow light. In some embodiments, an electrochromic medium containing a gray cathodic electroactive compound will allow at least 85%, at least 90%, or at least 95% of red light in the 620 to 750 nm range and at least 85%, at least 90%, or at least 95% of yellow light in the 570 to 590 nm range to be transmitted through the medium, provided there is/are no other compound(s) in the medium that absorb(s) the red light and/or yellow light.

Figure 1:
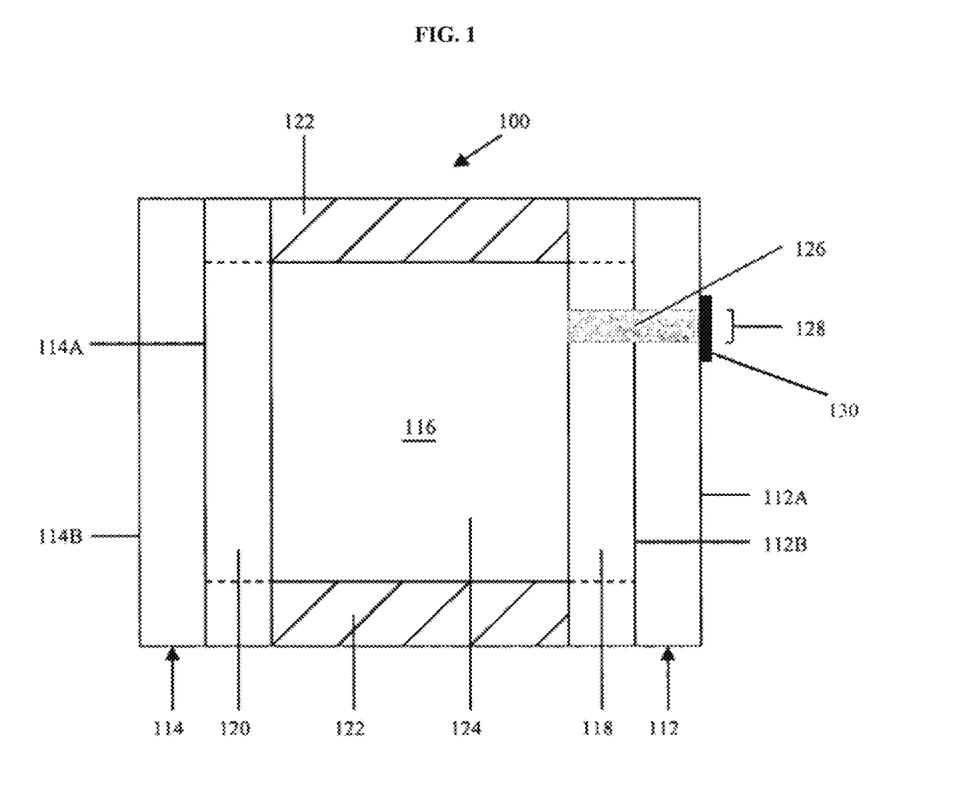
FIG. 1 is a cross-sectional schematic representation of an electrochromic device according to one embodiment.

Illustrative electrochromic device 100 may include, for illustrative purposes only, a window, an aircraft transparency, a mirror, a display device, and the like. It will be understood that like or analogous elements and/or components, and/or methods referred to herein, may be identified throughout the drawings with like reference characters. In some embodiments, the electrochromic device is an electrochromic window or an electrochromic mirror. In some embodiments, the device is a vehicular interior electrochromic mirror. In some embodiments, the device is a variable transmission electrochromic window. In some embodiments, the device is an aircraft window system. Other applications of the electrochromic device includes screens for watches, calculators and computer display screens; eye wear such as eyeglasses and sunglasses; switchable mirrors, sun visors; automobile, architectural, aircraft, marine, and spacecraft windows; information display boards and digital billboards and the like. It will be further understood that FIG. 1 is merely a schematic representation of electrochromic device 100. As such, some of the components have been distorted from their actual scale for pictorial clarity. Indeed, numerous other electrochromic device configurations are contemplated for use, including, but not limited to, those disclosed in U.S. Pat. Nos. 5,818,625; 6,597,489; and 6,700,692, all of which are hereby incorporated herein by reference in their entirety including all references incorporated therein.

In the device, the first substrate 112, having a front surface 112A and a rear surface 112B, may be fabricated from any of a number of materials that are transparent or substantially transparent in the visible region of the electromagnetic spectrum, such as, for example, borosilicate glass, soda lime glass, natural and synthetic polymeric resins, plastics, ceramics and/or composites including polyesters (e.g., PET), polyimides (PI), polycarbonates, polysulfones, polyethylene naphthalate (PEN), ethylene vinyl acetate (EVA), acrylate polymers, as well as Topas®, which is commercially available from Ticona of Summit, N.J. In some embodiments, the first substrate 112 may be fabricated from a sheet of glass having a thickness ranging from approximately 0.10 millimeters (mm) to approximately 12.7 mm. This may include where the thickness is from approximately 0.50 mm to approximately 1.50 mm, approximately 0.65 mm to approximately 1.00 mm, or approximately 0.75 mm to approximately 1.00 mm. Of course, the thickness of the substrate will depend largely upon the particular application of the electrochromic device. While particular substrate materials have been disclosed, for illustrative purposes only, it will be understood that numerous other substrate materials are likewise contemplated for use that exhibit appropriate physical properties, such as strength, to be able to operate effectively in conditions of intended use. Indeed, electrochromic devices may be, during normal operation, exposed to extreme temperature variation as well as substantial UV radiation, emanating primarily from the sun. It will be further understood that first substrate 112, second substrate 114, or both the first and second substrates may include a UV absorbing layer and/or contain a UV absorbing material to help protect the substrate(s) and/or the electrochromic media from UV damage.

Second substrate 114, having a front surface 114A and a rear surface 114B, may be fabricated from similar materials as that of first substrate 112. However, if the electrochromic device is a mirror, or the electrochromic device includes a mirrored surface, depending upon the surface that incorporates the mirror, the substrate may or may not be transparent. For example, the substrate may be transparent where the distal surface is the mirrored surface, and it may not be transparent where a proximal surface is mirrored. Accordingly, materials for use as the second substrate 114 may include polymers, metals, glass, and ceramics. Second substrate 114 is may be fabricated from a sheet of glass or plastic having a thickness ranging from approximately 0.10 mm to approximately 12.7 mm. This may include where the thickness is from approximately 0.50 mm to approximately 1.50 mm, approximately 0.65 mm to approximately 1.00 mm, or approximately 0.75 mm to approximately 1.00 mm. If first and second substrates 112 and 114, respectively, are fabricated from sheets of glass, then the glass can optionally be tempered, heat strengthened, chemically strengthened, and/or laminated prior to or subsequent to being coated with layers of electrically conductive material (118 and 120).

One or more layers of electrically conductive material 118 are associated with rear surface 112B of first substrate 112. These layers serve as an electrode for the electrochromic device. Electrically conductive material 118 is desirably a material that: (a) is substantially transparent in the visible region of the electromagnetic spectrum; (b) bonds reasonably well to first substrate 112; (c) maintains this bond when associated with a sealing member; (d) is generally resistant to corrosion from materials contained within the electrochromic device or the atmosphere; and (e) exhibits minimal diffuse or specular reflectance as well as sufficient electrical conductance. It is contemplated that electrically conductive material 118 may be fabricated from fluorine doped tin oxide (FTO), for example TEC glass, which is commercially available from Libbey Owens-Ford-Co., of Toledo, Ohio, indium/tin oxide (ITO), doped zinc oxide, indium zinc oxide, metal oxide/Ag/metal oxide, or other materials known to those having ordinary skill in the art.

One or more layers of electrically conductive material 120 made of the same or different materials as those associated with the rear surface 112B of the first substrate 112 may be associated with the front surface 114A of second substrate 114, and it may be operatively bonded to an electrically conductive material 118 by edge seal 122. As can be seen in FIG. 1, once bonded, edge seal 122, optional inner plug 126/fill port 128/outer plug 130, and the juxtaposed portions of electrically conductive materials 118 and 120 serve to generally define an inner peripheral geometry of chamber 116. Edge sealing techniques may be utilized which are disclosed in U.S. Pat. No. 7,372,611. In some embodiments, the device contains an epoxy sealing member (not shown).

Electrically conductive material 120 may vary depending upon the intended use of the electrochromic device. For example, if the electrochromic device is a mirror, then the material may include a transparent conductive coating similar to electrically conductive material 118 (in which case a reflector is associated with rear surface 114B of second substrate 114). Alternatively, electrically conductive material 120 may include a layer of reflective material as shown in U.S. Pat. No. 5,818,625. In this case, electrically conductive material 120 is associated with front surface 114A of second substrate 114. Typical coatings for this type of reflector include chromium, rhodium, ruthenium, silver, silver alloys, and combinations thereof.

In some embodiments, the cell spacing between inner surfaces of substrates 112 and 114 is from approximately 10 microns (µm) to approximately 750 µm. This includes where the cell spacing is from approximately 20 µm to approximately 600 µm, from approximately 100 µm to approximately 600 µm, from approximately 200 µm to approximately 600 µm, or from approximately 250 µm to approximately 450 µm. It will be understood that the thickness of the cell spacing will depend largely upon the particular application of the electrochromic device.

In some embodiments, the first substrate and second substrate have a cell distance of less than 700 µm. In another embodiment, the first substrate and second substrate have a cell distance of about 25 µm to about 100 µm, about 25 µm to about 90 µm, about 25 µm to about 80 µm, about 25 µm to about 70 µm, about 25 µm to about 150 µm, about 150 µm to about 700 µm, about 200 µm to about 600 µm, about 250 µm to about 500 µm, or ranges between any two of these values (including endpoints). In another embodiment, the first substrate and second substrate have a cell distance of about 700 µm, 650 µm, 600 µm, 550 µm, 500 µm, 450 µm, 400 µm, 350 µm, 300 µm, 275 µm, 250 µm, 225 µm, 200 µm, 175 µm, 150 µm, 125 µm, 100 µm, 95 µm, 90 µm, 85 µm, 80 µm, 75 µm, 70 µm, 65 µm, 60 µm, 55 µm, 50 µm, 45 µm, 40 µm, 35 µm, 30 µm, or 25 µm, or ranges between any two of these values (including endpoints).

In some embodiments, the electrochromic device 100 has a high transmittance when unpowered, or in other words in the absence of an applied potential. Conversely, when the electrochromic device is subjected to an applied potential it may have a low transmittance. In other words, unpowered, the electrochromic device allows light to pass, while in a low transmittance state light is absorbed. The amount of light that is transmitted or absorbed is dependent upon the types of substrates used and the properties of the electrochromic medium.

Sealing member 122 may include any material that is capable of being adhesively bonded to the electrically conductive materials 118 and 120 forming chamber 116, so that electrochromic medium 124 does not inadvertently leak out of the chamber (in certain embodiments in cooperation with a plug and fill port). As is shown in dashed lines in FIG. 1, it is also contemplated that the sealing member extend all the way to rear surface 112B and front surface 114A of their respective substrates. In such an embodiment, the layers of electrically conductive material 118 and 120 may be partially removed where the sealing member 122 is positioned. If electrically conductive materials 118 and 120 are not associated with their respective substrates, then sealing member 122 preferably bonds well to substrates 112 and 114, which may be comprised of glass. It will be understood that sealing member 122 can be fabricated from any one of a number of materials including, for example, those disclosed in U.S. Pat. Nos. 4,297,401; 4,418,102; 4,695,490; 5,596,023; 5,596,024; 6,157,480; and 6,714,334.

Electrochromic medium 124 includes at least one solvent, a blue cathodic electroactive compound and up to three anodic electroactive compounds. Typically, the cathodic and anodic electroactive compounds are electrochromic. It will be understood that regardless of its ordinary meaning, the term "electroactive" will be defined herein as a material or compound that undergoes a modification in its oxidation state upon exposure to a particular electrical potential difference. Additionally, it will be understood that the term "electrochromic" will be defined herein, regardless of its ordinary meaning, as a material or compound that exhibits a change in its extinction coefficient at one or more wavelengths upon exposure to a particular electrical potential difference.

In some embodiments, the concentration of the cathodic electroactive compounds in the electrochromic medium is from about 40 millimolar (mM) to about 500 mM. In some embodiments, the concentration of the cathodic electroactive compounds in the electrochromic medium is from about 40 mM to about 100 mM. In some embodiments, the concentration of the cathodic electroactive compounds in the electrochromic medium is from about 40 mM to about 80 mM.

In some embodiments, the total concentration of the cathodic electroactive compounds is at least about 40 mM. In some embodiments, the total concentration of the cathodic electroactive compounds is at least about 50 mM. This include concentrations of about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 mM, including increments therein. In some embodiments, the total concentration of the cathodic electroactive compounds is about 40 mM to about 100 mM, about 40 mM to about 90 mM, about 40 mM to about 80 mM, about 50 mM to about 100 mM, about 50 mM to about 90 mM, about 50 mM to about 80 mM, about 60 to about 90 mM, about 70 mM to about 80 mM, or ranges between any two of these values (including endpoints).

Cathodic electroactive compounds may include, but are not limited to, viologens. Illustrative viologens include, but are not limited to, 1,1'-bis-2-ethylhexyl-4,4-bipyridinium tetrafluoroborate (also called 2-ethylhexyl viologen tetrafluoroborate), methyl viologen tetrafluoroborate, octyl viologen tetrafluoroborate (octylviologen), and benzyl viologen tetrafluoroborate. Additional illustrative cathodic electroactive compounds include, but are not limited to, compounds disclosed in U.S. Pat. Nos. 7,046,418; 7,855,821; 4,902,108; 6,188,505; and 6,710,906. In some embodiments, the cathodic electroactive compounds include one or more alkyl viologens. Illustrative alkyl viologens include, but are not limited to, 2-ethylhexyl viologen tetrafluoroborate; methyl viologen tetrafluoroborate; octyl viologen tetrafluoroborate (octylviologen); 1,1'-bis-isobutyl-4,4'-bipyridinium tetrafluoroborate; and 1,1'-bis 2-ethyl butyl-4,4'-bipyridinium tetrafluoroborate. In some embodiments, the alkyl viologen is selected from 1,1'-bis-2-ethylhexyl-4,4-bipyridinium tetrafluoroborate, 1,1'-bis-isobutyl-4,4'-bipyridinium tetrafluoroborate; and 1,1'-bis 2-ethyl butyl-4,4'-bipyridinium tetrafluoroborate. Moreover, it is contemplated that the cathodic electroactive compounds may include a polymer film, such as polymeric viologens.

In some embodiments, the total concentration of the anodic electroactive compounds is at least about 40 mM. In some embodiments, the total concentration of the anodic electroactive compounds is at least about 50 mM. This include concentrations of about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 mM, including increments therein. In some embodiments, the total concentration of the anodic electroactive compounds is about 40 mM to about 100 mM, about 40 mM to about 90 mM, about 50 mM to about 100 mM, about 50 mM to about 90 mM, about 60 to about 90 mM, about 70 mM to about 80 mM, or ranges between any two of these values (including endpoints).

In some embodiments, the concentration of the green anodic electroactive compound is at least about 30 mM. In some embodiments, the concentration of the green anodic electroactive compound is at least about 40 mM. In some embodiments, the concentration of the green anodic electroactive compound is at least about 50 mM. This include concentrations of about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, and 80 mM, including increments therein. In some embodiments, the concentration of the green anodic electroactive compound is about 30 mM to about 80 mM, about 40 mM to about 80 mM, about 40 mM to about 70 mM, about 40 mM to about 60 mM, about 50 mM to about 70 mM, or ranges between any two of these values (including endpoints).

In some embodiments, the total concentration of the gray anodic electroactive compounds is less than about 16 mM. This includes concentrations of about 15, 14, 13, 12, 11, 10, 9, 8, 7, 6, 5, 4, 3, 2, and 1 mM, including increments therein. In some embodiments, the total concentration of the gray anodic electroactive compounds is about 2 mM to about 15 mM, about 2 mM to about 10 mM, about 2 mM to about 8 mM, about 5 mM to about 15 mM, about 5 mM to about 10 mM, or ranges between any two of these values (including endpoints). In some embodiments, at least one of the gray anodic electroactive compounds has a concentration of about 5 mM to about 7 mM. In some embodiments, at least one gray anodic electroactive compound has a concentration of about 5 mM to about 15 mM.

In some embodiments, the anodic electroactive compounds contain from about 5 mol % to about 15 mol % gray anodic electroactive compounds. This includes about 5, 6, 7, 8, 9, 10, 11, 12, 13, 14, and 15 mol %, including increments therein, gray anodic electroactive compounds. In some embodiments, the anodic electroactive compounds contain from about 8 mol % to about 15 mol % gray anodic electroactive compounds. This includes ranges of from about 8 mol % to about 14 mol %, from about 8 mol % to about 13 mol %, from about 8 mol % to about 12 mol %, from about 9 mol % to about 15 mol %, from about 9 mol % to about 14 mol %, and from about 9 mol % to about 13 mol % gray anodic electroactive compounds.

Illustrative anodic electroactive compounds may include, but are not limited to, ferrocene, substituted ferrocenes, phenazine, substituted phenazines, phenothiazine, substituted phenothiazines including substituted dithiazines, thianthrene, and substituted thianthrenes. Examples of anodic electroactive compounds may include di-tert-butyl-diethylferrocene, 5,10-dimethyl-5,10-dihydrophenazine (DMP), 3,7,10-trimethylphenothiazine, 2,3,7,8-tetramethoxy-thianthrene, 10-methylphenothiazine, tetramethylphenazine (TMP), bis(butyltriethylammonium)-para-methoxytriphenodithiazine (TPDT), polymer films such as polyaniline, polythiophene, and polymeric metallocenes, a solid transition metal oxides including, but not limited to, oxides of vanadium, nickel, iridium, as well as numerous heterocyclic compounds. It will be understood that numerous other anodic electroactive compounds are contemplated for use including those disclosed in U.S. Pat. Nos. 4,902,108; 6,188,505; and 6,710,906.

In some embodiments, the green electroactive compound is 5,10-dihydro-5,10-dineopentylphenazine; 5,10-isobutyl-5,10-dihydrophenazine; 5,10-[2(ethyl)butyl]-5,10-dihydrophenazine; or 5,10-[2(ethyl)hexyl]-5,10-dihydrophenazine. In some embodiments, the green electroactive compound is 5,10-dihydro-5,10-dineopentylphenazine.

In some embodiments, the gray electroactive compounds are selected from 2,7-diisobutyl-5,10-dineopentyl-5,10-dihydrophenazine; 2,7-di-2-ethylbutyl-5,10-dineopentyl-5,10-dihydrophenazine; 2,7-di-2-ethyl hexyl-5,10-dineopentyl-5,10-dihydrophenazine; and 2,5,7,10-tetraneopentyl-5,10-dihydrophenazine.

In some embodiments, the molar ratio of the cathodic electroactive compound to the anodic electroactive compounds is about 1:1 to about 1.1:1. In some embodiments, the molar ratio of the cathodic electroactive compound to the anodic electroactive compounds is about 1:1. In some embodiments, the molar ratio of the cathodic electroactive compound to the anodic electroactive compounds is about 1.1:1.

The electrochromic medium may include a single-layer of material which may include small non-homogenous regions and includes solution-phase devices where a material may be contained in solution in an ionically conducting electrolyte which remains in solution in the electrolyte when electrochemically oxidized or reduced. Solution phase electroactive materials may be contained in the continuous solution-phase of a gel medium as shown in U.S. Pat. No. 5,928,572, and in International Patent Application Serial No. PCT/US98/05570, both of which are hereby incorporated herein by reference in their entirety.

In some embodiments, a single-layer, single-phase medium includes a medium where the anodic and cathodic materials are incorporated into a polymer matrix as is described in International Patent Application Serial Nos. PCT/EP98/03862 and PCT/US98/05570.

The electrochromic medium may have a layered structure including a material attached directly to an electrically conducting electrode or confined in close proximity thereto which remains attached or confined when electrochemically oxidized or reduced. Alternatively, one or more materials in the electrochromic medium may undergo a change in phase during the operation of the device. For example, a material contained in solution in the ionically conducting electrolyte forms a layer on the electrically conducting electrode when electrochemically oxidized or reduced.

In addition, electrochromic medium 124 may include other materials, such as light absorbers, light stabilizers, thermal stabilizers, antioxidants, thickeners, viscosity modifiers, tint providing agents, redox buffers, and mixtures thereof. In some embodiments, the electrochromic medium further includes one or more UV stabilizers. In some embodiments, the electrochromic medium further includes an anodic and/or cathodic color-stabilizing redox buffer. In some embodiments, the electrochromic medium further includes a cross-linked polymer matrix, a free-standing gel, and/or a substantially non-weeping gel. Suitable redox buffers include, among others, those disclosed in U.S. Pat. No. 6,188,505. Suitable UV-stabilizers may include, but are not limited to, 2-ethyl-2-cyano-3,3-diphenyl acrylate (Uvinul® N-35 or Viosorb® 910), (2-ethylhexyl)-2-cyano-3,3-diphenyl acrylate (Uvinul® N-539), 2-(2'-hydroxy-4'-methylphenyl)benzotriazole (Tinuvin® P), 3-[3-(2H-benzotriazole-2-yl)-5-(1,1-dimethylethyl)-4-hydroxyphenyl]propionic acid pentyl ester (prepared from Tinuvin® 213 via conventional hydrolysis followed by conventional esterification; hereinafter referred to as "Tinuvin PE"); a composition of $C_{7-9}$ branched and linear alkyl esters of 3-(2H-benzotriazol-2-yl)-5-(1,1-dimethylethyl)-4-hydroxy-benzenepropanoic acid and 1-methoxy-2-propylacetate (Tinuvin® 384-2); 2,4-dihydroxybenzophenone; 2-hydroxy-4-methoxybenzophenone (Cyasorb® UV 9), and 2-ethyl-2'-ethoxyalanilide (Sanduvor® VSU). In some embodiments, the electrochromic medium 124 contains at least one crosslinked gel matrix. In some embodiments, the electrochromic medium 124 contains at least one crosslinked gel matrix and at least one solvent.

Illustrative solvents for use in the electrochromic medium may include, but are not limited to, 3-methylsulfolane, dimethyl sulfoxide, dimethyl formamide, tetraglyme and other polyethers; alcohols such as ethoxyethanol; nitriles, such as acetonitrile, glutaronitrile, 3-hydroxypropionitrile, and 2-methylglutaronitrile; ketones including 2-acetylbutyrolactone, and cyclopentanone; cyclic esters including beta-propiolactone, gamma-butyrolactone, and gamma-valerolactone; propylene carbonate (PC), ethylene carbonate; and homogenous mixtures of the same. While specific solvents have been disclosed as being associated with the electrochromic medium, numerous other solvents that would be known to those having ordinary skill in the art having the present disclosure before them are likewise contemplated for use.

The u'-v' color space exhibited by the electrochromic devices, disclosed herein, when in a low transmission state, may exhibit a u' value from 0.15 to 0.30 and a v' value from 0.30 to 0.40. In some embodiments, the u' value is from about 0.15 to about 0.27, from about 0.15 to about 0.25, from about 0.15 to about 0.22, from about 0.15 to about 0.20, from about 0.18 to about 0.30, from about 0.18 to about 0.27, from about 0.18 to about 0.25, from about 0.18 to about 0.22, or from about 0.18 to about 0.20. In some embodiments, the u' value is about 0.15, 0.16, 0.17, 0.18, 0.19, 0.20, 0.21, 0.22, 0.23, 0.24, 0.25, 0.26, 0.27, 0.28, 0.29, or 0.30, including increments therein. In some embodiments, the v' value is from about 0.30 to about 0.37, from about 0.30 to about 0.35, from about 0.30 to about 0.33, from about 0.33 to about 0.40, from about 0.33 to about 0.37, from about 0.33 to about 0.35, or from about 0.35 to about 0.40. In some embodiments, the v' value is about 0.30, 0.31, 0.32, 0.33, 0.34, 0.35, 0.36, 0.37, 0.38, 0.39, or 0.40, including increments therein. In some embodiments, the u' value is from about 0.18 to about 0.22 and the v' value is from 0.30 to 0.40.

Provided herein, in another aspect, are methods to minimize or remove purple hue from an electrochromic medium within an electrochromic device in the darkened state, the method including adjusting the concentration of gray anodic electroactive compound to from about 8 mol % to about 15 mol % relative to the total molar concentration of anodic electroactive compounds. In some embodiments, the concentration of gray anodic electroactive compound is adjusted to from about 8 mol % to about 13 mol % relative to the total molar concentration of anodic electroactive compounds. In some embodiments, the concentration of gray anodic electroactive compound is adjusted to from about 10 mol % to about 12 mol % relative to the total molar concentration of anodic electroactive compounds.

The present invention, thus generally described, will be understood more readily by reference to the following examples, which are provided by way of illustration and are not intended to be limiting of the present invention.

EXAMPLES

Comparative Example 1

A variable transmission electrochromic device was prepared by placing two indium tin oxide (ITO)-coated glass substrates spaced 250 μm apart in a parallel arrangement with the ITO coated sides facing each other. Each substrate had a conductive silver epoxy dispensed around the perimeter of the substrate. An epoxy seal was dispensed around the perimeter extending inward of the silver epoxy, between the two substrates, sealing the substrates together to form a chamber. The epoxy seal was allowed to cure. The chamber was then filled with an electrochromic composition in propylene carbonate. Included in the composition were 69.6 mM 1,1'-bis-2-ethylhexyl-4,4-bipyridinium tetrafluoroborate; 53.0 mM 5,10-dihydro-5,10-dineopentylphenazine; 5.8 mM 2,7-di-2-ethylbutyl-5,10-dineopentyl-5,10-dihydrophenazine; 5.8 mM 2,7-diisobutyl-5,10-dineopentyl-5,10-dihydrophenazine; 15 mM Tinuvin 384; 30 mM Tinuvin PE; 170 mM 4-methoxy-2-hydroxy benzophenone; 1.0 mM decamethyl ferrocinium $BF_4$; 0.5 mM decamethyl ferrocene. The composition was formed into a cross-linked polymer matrix as described in U.S. Pat. No. 6,635,194, where the polymer matrix was made from a 5.5% by weight polymer made from 2-hydroxyethyl methacrylate and methylacrylate at a 1:10 molar ratio, respectively, and cross-linked with 0.375% by weight 4,4'-methylenebis(phenyl isocyanate) (MDI) and catalyzed with 8 ppm dibutyltin diacetate. Upon darkening of this device, the observed color at room temperature was noticeably purple.

Example 2

A variable transmission electrochromic device was prepared by placing two indium tin oxide (ITO)-coated glass substrates spaced 250 μm apart in a parallel arrangement with the ITO coated sides facing each other. Each substrate had a conductive silver epoxy dispensed around the perimeter of the substrate. An epoxy seal was dispensed around the perimeter extending inward of the silver epoxy, between the two substrates, sealing the substrates together to form a chamber. The epoxy seal was allowed to cure. The chamber was then filled with an electrochromic composition in propylene carbonate. Included in the composition were 69.6 mM 1,1'-bis-2-ethylhexyl-4,4-bipyridinium tetrafluoroborate; 55.9 mM 5,10-dihydro-5,10-dineopentyl phenazine; 5.8 mM 2,7-di-2-ethylbutyl-5,10-dineopentyl-5,10-dihydrophenazine; 2.9 mM 2,7-diisobutyl-5,10-dineopentyl-5,10-dihydrophenazine; 15 mM Tinuvin 384; 30 mM Tinuvin PE; 170 mM 4-methoxy-2-hydroxy benzophenone; 1.0 mM decamethyl ferrocinium $BF_4$; 0.5 mM decamethyl ferrocene. The composition was formed into a cross-linked polymer matrix as described in U.S. Pat. No. 6,635,194, where the polymer matrix was made from a 5.5% by weight polymer made from 2-hydroxyethyl methacrylate and methylacrylate at a 1:10 molar ratio, respectively, and cross-linked with 0.375% by weight 4,4'-methylenebis(phenyl isocyanate) (MDI) and catalyzed with 8 ppm dibutyltin diacetate. Upon darkening of this device, the color was more neutral than the device of Comparative Example 1.

Example 3

A variable transmission electrochromic device was prepared by placing two indium tin oxide (ITO)-coated glass substrates spaced 250 μm apart in a parallel arrangement with the ITO coated sides facing each other. Each substrate had a conductive silver epoxy dispensed around the perimeter of the substrate. An epoxy seal was dispensed around the perimeter extending inward of the silver epoxy, between the two substrates, sealing the substrates together to form a chamber. The epoxy seal was allowed to cure. The chamber was then filled with an electrochromic composition in propylene carbonate. Included in the composition were 69.6 mM 1,1'-bis-2-ethylhexyl-4,4-bipyridinium tetrafluoroborate; 55.2 mM 5,10-dihydro-5,10-dineopentyl phenazine; 5.8 mM 2,7-di-2-ethylbutyl-5,10-dineopentyl-5,10-dihydrophenazine; 3.6 mM 2,7-diisobutyl-5,10-dineopentyl-5,10-dihydrophenazine; 15 mM Tinuvin 384; 30 mM Tinuvin PE; 170 mM 4-methoxy-2-hydroxy benzophenone; 1.0 mM decamethyl ferrocinium $BF_4$; 0.5 mM decamethyl ferrocene. The composition was formed into a cross-linked polymer matrix as described in U.S. Pat. No. 6,635,194, where the polymer matrix was made from a 5.5% by weight polymer made from 2-hydroxyethyl methacrylate and methylacrylate at a 1:10 molar ratio, respectively, and cross-linked with 0.375% by weight 4,4'-methylenebis(phenyl isocyanate) (MDI) and catalyzed with 8 ppm dibutyltin diacetate. Upon darkening of this device, the color was more neutral than the device of Comparative Example 1.

Example 4

Seven 5"×5" electrochromic windows made in a similar fashion as the devices of Examples 1-3, using 54.4 mM 1,1'-bis-2-ethylhexyl-4,4-bipyridinium tetrafluoroborate and varying concentrations of anodic materials as shown in the following table:

| Entry | 5,10-dihydro-5,10-dineopentyl phenazine | 2,7-di-2-ethylbutyl-5,10-dineopentyl-5,10-dihydrophenazine |
|---|---|---|
| A | 44.7 mM | 7.0 mM |
| B | 45.2 mM | 6.5 mM |
| C | 45.7 mM | 6.0 mM |
| D | 46.1 mM | 5.6 mM |
| E | 46.6 mM | 5.1 mM |
| F | 42.4 mM | 9.3 mM |
| G | 51.7 mM | none |

Figure 2:
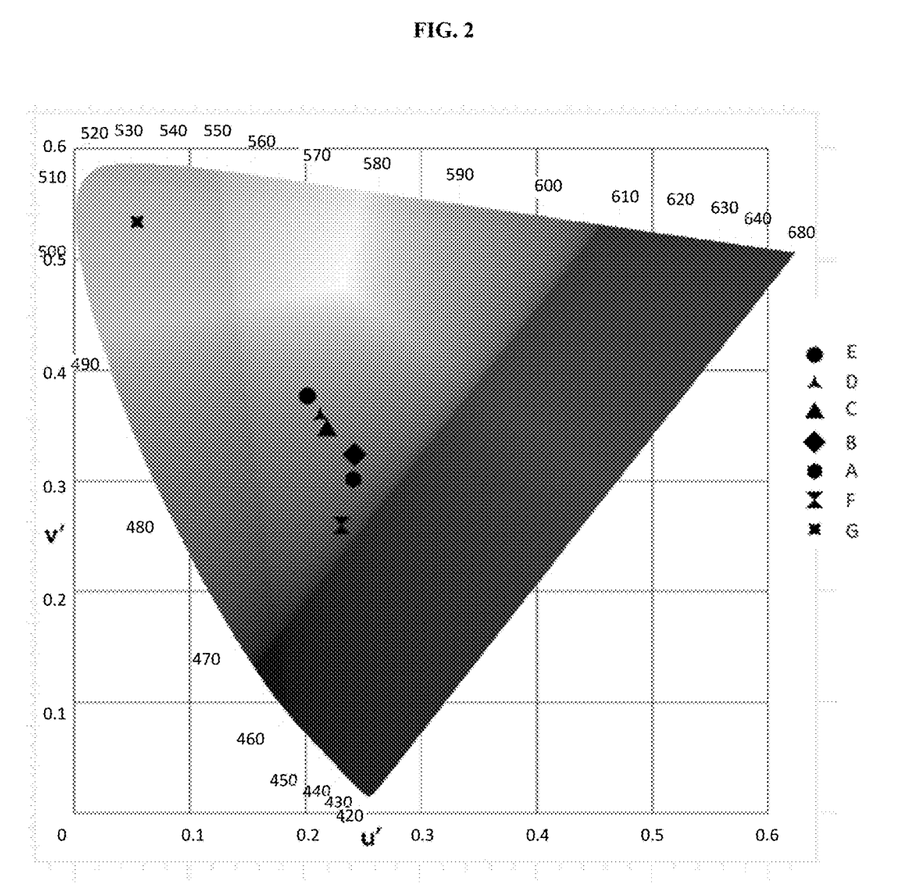
FIG. 2 depicts visual spectra of non-limiting examples of electrochromic devices darkened at 1.2 V.

Entries A-E are non-limiting examples of the technology described herein. Entries F and G are comparative examples (controls). The windows were darkened at 1.2 V, and the visual spectra were recorded. The results (u'-v' color space) are shown in FIG. 2. In particular, the coordinates for Entry E are u' 0.2024, v' 0.3772; the coordinates for Entry D are u' 0.2131, v' 0.3595; and the coordinates for Entry C are u' 0.2189, v' 0.3457.

Example 5

Five 5"×5" electrochromic windows were made in a similar fashion as the devices of Example 4, using 5,10-dihydro-5,10-dineopentyl-2,7-[2-(ethyl) butyl] phenazine (gray anodic electroactive compound); 5,10-dihydro-5,10-dineopentyl phenazine (green anodic electroactive compound); and 1,1'-[2-(ethyl)hexyl]-4,4'-dipyridinium bis-tetrafluoroborate (alkyl viologen). The concentration of the gray anodic electroactive compound was varied (55% to 75%) relative to the concentration of gray anodic electroactive compound used in a control device with larger cell spacing (containing 34.8 mM viologen, 26.5 mM green anodic electroactive compound and 5.8 mM gray anodic electroactive compound).

| Entry* | green anodic electroactive compound (mM) | gray anodic electroactive compound (mM) | Gray anodic electroactive compound content relative to control |
|---|---|---|---|
| A | 46.6 | 5.1 | 55% |
| B | 46.1 | 5.6 | 60% |
| C | 45.7 | 6.0 | 65% |
| D | 45.2 | 6.5 | 70% |
| E | 44.7 | 7.0 | 75% |

*All windows contained 54.4 mM of 1,1'-[2-(ethyl)hexyl]-4,4'-dipyridinium bis-tetrafluoroborate.

Figure 3:
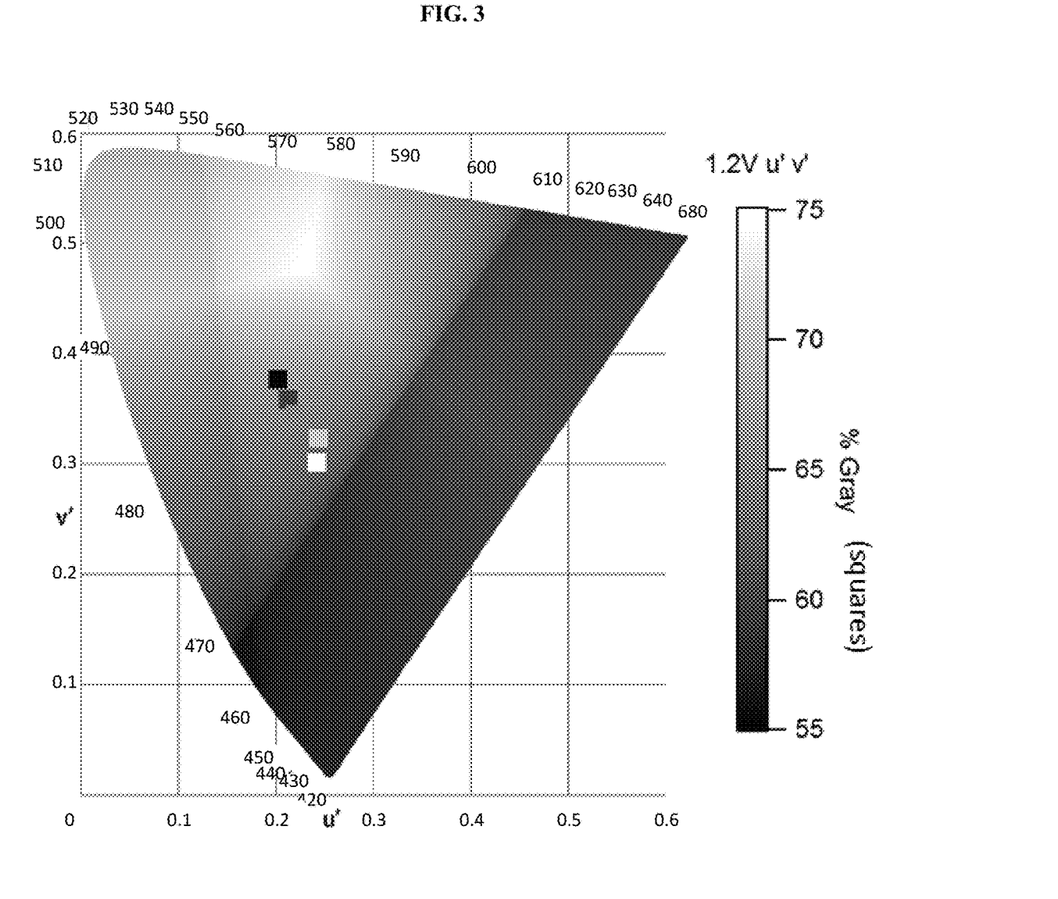
FIG. 3 depicts visual spectra of non-limiting examples of electrochromic devices darkened at 1.2 V.

The windows were darkened at 1.2 V, and the visual spectra were recorded. The results (u'-v' color space) are shown in FIG. 3. Based on these data and visual inspection by the naked eye, the window with 60% gray anodic electroactive compound relative to control was selected as yielding the most similar blue-gray color as the control device. The coordinates for u' is 0.21308, v' is 0.359478.

Para. A.

An electrochromic device comprising:

a chamber defined by a first conductive surface of a first substrate, a second conductive surface of a second substrate, and a sealing member joining the first substrate to the second substrate;

an electrochromic medium comprising a blue cathodic electroactive compound and up to three anodic electroactive compounds;

wherein the electrochromic medium is disposed within the chamber;

the anodic electroactive compounds comprise a green anodic electroactive compound and one or two gray anodic electroactive compounds; and the anodic electroactive compounds comprise from about 8 mol % to about 15 mol % gray anodic electroactive compounds.

Para. B.

The electrochromic device of Para. A, wherein the anodic electroactive compounds comprise one green anodic electroactive compound and two gray anodic electroactive compounds.

Para. C.

The electrochromic device of Para. A or Para. B, wherein the gray anodic electroactive compounds are selected from 2,7-diisobutyl-5,10-dineopentyl-5,10-dihydrophenazine; 2,7-di-2-ethylbutyl-5,10-dineopentyl-5,10-dihydrophenazine; 2,7-di-2-ethylhexyl-5,10-dineopentyl-5,10-dihydrophenazine; and 2,5,7,10-tetraneopentyl-5,10-dihydrophenazine.

Para. D.

The electrochromic device of any one of Paras. A-C, wherein the blue cathodic electroactive compound is an alkyl viologen.

Para. E.

The electrochromic device of Para. D, wherein the alkyl viologen is selected from 1,1'-bis-2-ethylhexyl-4,4-bipyridinium tetrafluoroborate, 1,1'-bis-isobutyl-4,4'-bipyridinium tetrafluoroborate; and 1,1'-bis 2-ethyl butyl-4,4'-bipyridinium tetrafluoroborate.

Para. E.

The electrochromic device of any one of Paras. A-E, wherein the green anodic electroactive compound is 5,10-dihydro-5,10-dineopentylphenazine; 5,10-[2(ethyl)butyl]-5,10-dihydrophenazine; or 5,10-[2(ethyl)hexyl]-5,10-dihydro phenazine.

Para. G.

The electrochromic device of any one of Paras. A-F, wherein the molar ratio of the cathodic electroactive compound to the anodic electroactive compounds is about 1:1 to about 1.1:1.

Para. H.

The electrochromic device of any one of Paras. A-G, further comprising one or more UV stabilizers.

Para. I.

The electrochromic device of Para. H, wherein the one or more UV stabilizers are selected from 2-ethyl-2-cyano-3,3-diphenyl acrylate; (2-ethylhexyl)-2-cyano-3,3-diphenyl acrylate; 2-(2'-hydroxy-4'-methylphenyl)benzotriazole; 3-[3-(2H-benzotriazole-2-yl)-5-(1,1-dimethylethyl)-4-hydroxyphenyl]propionic acid pentyl ester; a composition of $C_{7-9}$ branched and linear alkyl esters of 3-(2H-benzotriazol-2-yl)-5-(1,1-dimethylethyl)-4-hydroxy-benzenepropanoic acid and 1-methoxy-2-propylacetate; 2,4-dihydroxybenzophenone; 2-hydroxy-4-methoxybenzophenone; and 2-ethyl-2'-ethoxyalanilide.

Para. J.

The electrochromic device of any one of Paras. A-I, further comprising an anodic and/or cathodic color-stabilizing redox buffer.

Para. K.

The electrochromic device of any one of Paras. A-J, further comprising a cross-linked polymer matrix, a free-standing gel, and/or a substantially non-weeping gel.

Para. L.

The electrochromic device of any one of Paras. A-K, wherein the electrochromic device has a clear state and a darkened state and the electrochromic medium maintains a blue-gray color in the darkened state.

Para. M.

The electrochromic device of Para. L, wherein the blue-gray color is devoid of a purple hue as observed by the naked eye.

Para. N.

The electrochromic device of any one of Paras. A-M, wherein the electrochromic device is an electrochromic aircraft transparency.

Para. O.

A method to minimize or remove purple hue from an electrochromic medium within an electrochromic device in the darkened state, the method comprising adjusting the concentration of gray anodic electroactive compound to from about 8 mol % to about 15 mol % relative to the total molar concentration of anodic electroactive compounds.

Para. P.

The method of Para. O, wherein the gray anodic electroactive compound comprises one or more selected from 2,7-diisobutyl-5,10-dineopentyl-5,10-dihydrophenazine; 2,7-di-2-ethylbutyl-5,10-dineopentyl-5,10-dihydrophenazine; 2,7-di-2-ethylhexyl-5,10-dineopentyl-5,10-dihydrophenazine; and 2,5,7,10-tetraneopentyl-5,10-dihydrophenazine.

Para. Q.

An electrochromic device comprising:
a chamber defined by a first conductive surface of a first substrate, a second conductive surface of a second substrate, and a sealing member joining the first substrate to the second substrate;
an electrochromic medium comprising a blue cathodic electroactive compound and up to three anodic electroactive compounds;
wherein
the electrochromic medium is disposed within the chamber;
the anodic electroactive compounds comprise a green anodic electroactive compound and one or two gray anodic electroactive compounds; and
the anodic electroactive compounds comprise from about 8 mol % to about 15 mol % gray anodic electroactive compounds.

Para. R.

The electrochromic device of Para. Q, wherein the electrochromic device, in a low transmission state, exhibits a u'-v' color space where a u' value is from about 0.15 to about 0.30 and a v' value is from about 0.30 to about 0.40.

Para. S.

The electrochromic device of Para. R, wherein the u' value is from about 0.18 to about 0.22.

Para. T.

An electrochromic device comprising an electrochromic medium comprising a blue cathodic electroactive compound and up to three anodic electroactive compounds;
wherein:
the anodic electroactive compounds comprise a green anodic electroactive compound and one or two gray anodic electroactive compounds; and
the electrochromic device exhibits, in a low transmission state, a u'-v' color space wherein a u' value is from about 0.15 to about 0.30 and a v' value is from about 0.30 to about 0.40.

Para. U.

The electrochromic device of Para. T, wherein the u' value is from about 0.18 to about 0.22.

Para. V.

The electrochromic device of any one of Paras. Q-U, wherein the anodic electroactive compounds comprise one green anodic electroactive compound and two gray anodic electroactive compounds.

Para. W.

The electrochromic device of any one of Paras. Q-U, wherein the gray anodic electroactive compounds are selected from 2,7-diisobutyl-5,10-dineopentyl-5,10-dihydrophenazine; 2,7-di-2-ethylbutyl-5,10-dineopentyl-5,10-dihydrophenazine; 2,7-di-2-ethylhexyl-5,10-dineopentyl-5,10-dihydrophenazine; and 2,5,7,10-tetraneopentyl-5,10-dihydrophenazine.

Para. X.

The electrochromic device of any one of Paras. Q-W, wherein the blue cathodic electroactive compound is an alkyl viologen.

Para. Y.

The electrochromic device of Para. X, wherein the alkyl viologen is selected from 1,1'-bis-2-ethylhexyl-4,4-bipyridinium tetrafluoroborate, 1,1'-bis-isobutyl-4,4'-bipyridinium tetrafluoroborate; and 1,1'-bis 2-ethyl butyl-4,4'-bipyridinium tetrafluoroborate.

Para. Z.

The electrochromic device of any one of Paras. Q-Y, wherein the green anodic electroactive compound is 5,10-dihydro-5,10-dineopentylphenazine; 5,10-[2(ethyl)butyl]-5,10-dihydrophenazine; or 5,10-[2(ethyl)hexyl]-5,10-dihydrophenazine.

Para. AA.

The electrochromic device of any one of Paras. Q-Z, wherein the molar ratio of the cathodic electroactive compound to the anodic electroactive compounds is about 1:1 to about 1.1:1.

Para. AB.

The electrochromic device of any one of Paras. Q-AA, further comprising one or more UV stabilizers.

Para. AC.

The electrochromic device of Para. AB, wherein the one or more UV stabilizers are selected from 2-ethyl-2-cyano-3,3-diphenyl acrylate; (2-ethylhexyl)-2-cyano-3,3-diphenyl acrylate; 2-(2'-hydroxy-4'-methylphenyl)benzotriazole; 3-[3-(2H-benzotriazole-2-yl)-5-(1,1-dimethylethyl)-4-hydroxyphenyl]propionic acid pentyl ester; a composition of $C_{7-9}$ branched and linear alkyl esters of 3-(2H-benzotriazol-2-yl)-5-(1,1-dimethylethyl)-4-hydroxy-benzenepropanoic acid and 1-methoxy-2-propylacetate; 2,4-dihydroxybenzophenone; 2-hydroxy-4-methoxybenzophenone; and 2-ethyl-2'-ethoxyanilide.

Para. AD.

The electrochromic device of any one of Paras. Q-AC, further comprising an anodic and/or cathodic color-stabilizing redox buffer.

Para. AE.

The electrochromic device of any one of Paras. Q-AD, further comprising a cross-linked polymer matrix, a free-standing gel, and/or a substantially non-weeping gel.

Para. AF.

The electrochromic device of any one of Paras. Q-AE, wherein the electrochromic device has a clear state and a darkened state and the electrochromic medium maintains a blue-gray color in the darkened state.

Para. AG.

The electrochromic device of Para. AF, wherein the blue-gray color is devoid of a purple hue as observed by the naked eye.

Para. AH.

The electrochromic device of any one of Paras. Q-AG, wherein the electrochromic device is an electrochromic aircraft transparency.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.
What is claimed is:

1. An electrochromic device comprising:
a chamber defined by a first conductive surface of a first substrate, a second conductive surface of a second substrate, and a sealing member joining the first substrate to the second substrate;
an electrochromic medium comprising a blue cathodic electroactive compound and up to three anodic electroactive compounds;
wherein
the electrochromic medium is disposed within the chamber;
the anodic electroactive compounds comprise a green anodic electroactive compound and one or two gray anodic electroactive compounds; and
the anodic electroactive compounds comprise from about 8 mol % to about 15 mol % gray anodic electroactive compounds.

2. The electrochromic device of claim 1, wherein the anodic electroactive compounds comprise one green anodic electroactive compound and two gray anodic electroactive compounds.

3. The electrochromic device of claim 1, wherein the gray anodic electroactive compounds are selected from 2,7-di-isobutyl-5,10-dineopentyl-5,10-dihydrophenazine; 2,7-di-2-ethylbutyl-5,10-dineopentyl-5,10-dihydrophenazine; 2,7-di-2-ethylhexyl-5,10-dineopentyl-5,10-dihydrophenazine; and 2,5,7,10-tetraneopentyl-5,10-dihydrophenazine.

4. The electrochromic device of claim 1, wherein the blue cathodic electroactive compound is an alkyl viologen.

5. The electrochromic device of claim 4, wherein the alkyl viologen is selected from 1,1'-bis-2-ethylhexyl-4,4-bipyridinium tetrafluoroborate, 1,1'-bis-isobutyl-4,4'-bipyridinium tetrafluoroborate; and 1,1'-bis 2-ethyl butyl-4,4'-bipyridinium tetrafluoroborate.

6. The electrochromic device of claim 1, wherein the green anodic electroactive compound is 5,10-dihydro-5,10-dineopentylphenazine; 5,10-[2(ethyl)butyl]-5,10-dihydrophenazine; or 5,10-[2(ethyl)hexyl]-5,10-dihydro phenazine.

7. The electrochromic device of claim 1, wherein the molar ratio of a cathodic electroactive compound to the anodic electroactive compounds is about 1:1 to about 1.1:1.

8. The electrochromic device of claim 1, further comprising one or more UV stabilizers.

9. The electrochromic device of claim 8, wherein the one or more UV stabilizers are selected from 2-ethyl-2-cyano-3,3-diphenyl acrylate; (2-ethylhexyl)-2-cyano-3,3-diphenyl acrylate; 2-(2'-hydroxy-4'-methylphenyl)benzotriazole; 3-[3-(2H-benzotriazole-2-yl)-5-(1,1-dimethylethyl)-4-hydroxyphenyl]propionic acid pentyl ester; a composition of $C_{7-9}$ branched and linear alkyl esters of 3-(2H-benzotriazol-2-yl)-5-(1,1-dimethylethyl)-4-hydroxy-benzenepropanoic acid and 1-methoxy-2-propylacetate; 2,4-dihydroxybenzophenone; 2-hydroxy-4-methoxybenzophenone; and 2-ethyl-2'-ethoxyalanilide.

10. The electrochromic device of claim 1, further comprising an anodic and/or cathodic color-stabilizing redox buffer.

11. The electrochromic device of claim 1, further comprising a cross-linked polymer matrix, a free-standing gel, and/or a substantially non-weeping gel.

12. The electrochromic device of claim 1, wherein the electrochromic device has a clear state and a darkened state and the electrochromic medium maintains a blue-gray color in the darkened state.

13. The electrochromic device of claim 12, wherein the blue-gray color is devoid of a purple hue as observed by the naked eye.

14. The electrochromic device of claim 1, wherein the electrochromic device is an electrochromic aircraft transparency.

15. The electrochromic device of claim 1, wherein the electrochromic device, in a low transmission state, exhibits a u'-v' color space where a u' value is from about 0.15 to about 0.30 and a v' value is from about 0.30 to about 0.40.

16. The electrochromic device of claim 15, wherein the u' value is from about 0.18 to about 0.22.

17. A method to minimize or remove purple hue from an electrochromic medium within an electrochromic device in a darkened state, the method comprising adjusting a concentration of gray anodic electroactive compound of the electrochromic medium to from about 8 mol % to about 15 mol % relative to a total molar concentration of anodic electroactive compounds of the electrochromic medium.

18. The method of claim 17, wherein the gray anodic electroactive compound comprises one or more selected from 2,7-diisobutyl-5,10-dineopentyl-5,10-dihydrophenazine; 2,7-di-2-ethylbutyl-5,10-dineopentyl-5,10-dihydrophenazine; 2,7-di-2-ethylhexyl-5,10-dineopentyl-5,10-dihydrophenazine; and 2,5,7,10-tetraneopentyl-5,10-dihydrophenazine.

19. An electrochromic device comprising an electrochromic medium comprising a blue cathodic electroactive compound and up to three anodic electroactive compounds;
wherein:
the anodic electroactive compounds comprise a green anodic electroactive compound and one or two gray anodic electroactive compounds; and
the electrochromic device exhibits, in a low transmission state, a u'-v' color space wherein a u' value is from about 0.15 to about 0.30 and a v' value is from about 0.30 to about 0.40.

20. The electrochromic device of claim 19, wherein the u' value is from about 0.18 to about 0.22.

* * * * *